United States Patent
Shelley et al.

(10) Patent No.: US 6,784,431 B2
(45) Date of Patent: Aug. 31, 2004

(54) METHOD OF MEASURING ANODIZE COATING AMOUNT USING INFRARED ABSORBANCE

(75) Inventors: Paul H. Shelley, Lakewood, WA (US); Linda A. Caldwell Stancin, Renton, WA (US); Kathryn A. Soucy, Seattle, WA (US)

(73) Assignee: The Boeing Company, Chicago, IL (US)

( * ) Notice: Subject to any disclaimer, the term of this patent is extended or adjusted under 35 U.S.C. 154(b) by 94 days.

(21) Appl. No.: 10/171,579

(22) Filed: Jun. 13, 2002

(65) Prior Publication Data

US 2003/0230718 A1 Dec. 18, 2003

(51) Int. Cl.$^7$ .............................................. G01N 21/35
(52) U.S. Cl. ................... 250/341.8; 250/338.1
(58) Field of Search ....................... 250/341.8, 341.1, 250/338.1, 339.01

(56) References Cited

U.S. PATENT DOCUMENTS

| | | |
|---|---|---|
| 3,017,512 A | 1/1962 | Wolbert |
| 3,973,122 A | 8/1976 | Goldberg |
| 3,994,586 A | 11/1976 | Sharkins et al. |
| 4,015,127 A * | 3/1977 | Sharkins ..................... 250/341 |
| 4,549,079 A | 10/1985 | Terasaka et al. |
| 4,791,296 A | 12/1988 | Carpio |
| 4,800,279 A | 1/1989 | Hieftje et al. |
| 5,015,856 A | 5/1991 | Gold |
| 5,381,228 A | 1/1995 | Brace |
| 6,052,191 A | 4/2000 | Brayden, Jr. et al. |

FOREIGN PATENT DOCUMENTS

| | | |
|---|---|---|
| DE | 2252527 | 10/1972 |
| WO | WO 01/92820 A1 | 12/2001 |

OTHER PUBLICATIONS

Kumar, C. Siva et al., "Studies on anodic oxide coating with low absorptance and high emittance on aluminum alloy 2024", Solar Energy Material & Solar Cells 60 (2000) p. 51–57, Received Feb. 22, 1999, received in revised form Apr. 12, 1999, accepted Jun. 1, 1999, www.elsevier.com.

Kumar, C. Siva et al., "Studies on white anodizing on aluminum alloy for space applications", Applied Surface Science 151 (1999) p. 280–286, Received Mar. 20, 1999, accepted May 31, 1999, www.elsevier.nl/locate/apsusc.

* cited by examiner

*Primary Examiner*—Constantine Hannaher
*Assistant Examiner*—Timothy J. Moran
(74) *Attorney, Agent, or Firm*—Black Lowe & Graham PLLC; Mark S. Beaufait

(57) ABSTRACT

A non-destructive method is provided for determining the amount of an anodize coating on a metallic substrate. A value of infrared energy reflected from the metallic substrate without the anodize coating is determined. A value of infrared energy reflected from the metallic substrate with the anodize coating is determined. A value of infrared energy absorbed in the anodize coating is determined, and the value of the infrared energy absorbed in the anodize coating is correlated to an amount of the anodize coating.

24 Claims, 4 Drawing Sheets

METHOD OF MEASURING ANODIZE COATING AMOUNT USING INFRARED ABSORBANCE

RELATED APPLICATIONS

This patent application is related to a concurrently-filed patent application entitled "Method of Measuring Sol-Gel Coating Thickness Using Infrared Absorbance" and having application Ser. No. 10/171,180 and to a concurrently-filed patent application entitled "Method of Measuring Chromated Conversion Coating Amount Using Infrared Absorbance" and having application Ser. No. 10/171,182, both of which are hereby incorporated by reference.

FIELD OF THE INVENTION

This invention relates generally to measuring coating amount and, more specifically to measuring coating amount on metal surfaces.

BACKGROUND OF THE INVENTION

Anodized coatings are created upon metallic substrates for a great variety of purposes. For example, aluminum aircraft parts often receive an anodized coating for corrosion resistance and for enhanced paint adhesion. Anodize coatings are also used for decorative purposes. Generally, a uniform coating amount or a coating amount within an acceptable range is desired. However, determining uniformity of the coating amount or quantifying the coating amount relative to a desired range may be difficult. Current coating amount testing methods are destructive and therefore cannot be used with final production products. They are also time consuming, environmentally unfriendly, and disruptive to large scale production processes. Anodize coating amount is sometimes specified for some applications and there is no simple non-destructive evaluation for measurement of anodize amount currently known in the art.

Current coating amount testing known in the art is performed by measuring the weight of a coated metallic test specimen. The coating is then chemically removed from the specimen. The metallic substrate is reweighed and the difference is the amount of the anodized coating, which is normally given in milligrams per square foot (mg/ft2). Because the test method is destructive, it cannot be used on the manufactured product. In addition, the currently known testing process only generates a spatially averaged coating amount for the sample. As such, the currently known testing process does not determine coating amount variations over an area.

Therefore, there exists an unmet need in the art for a nondestructive means of testing anodized coating amount on a metallic substrate.

SUMMARY OF THE INVENTION

The present invention provides a nondestructive method for efficiently determining the amount of an anodize coating formed upon a metallic substrate without stripping the anodize coating from the metallic substrate. The "amount" of coating may represent either a coating thickness or weight. The invention may be employed in an in-line production facility or may be used intermittently as desired. The process may be used to provide a quantitative measurement, such as actual coating amount, or a qualitative measurement, such as a go or no-go result.

According to one embodiment of the invention, a nondestructive method is provided for determining the amount of an anodize coating on a metallic substrate. A value of infrared energy reflected from the metallic substrate without the anodize coating is determined. A value of infrared energy reflected from the metallic substrate with the anodize coating is determined. A value of infrared energy absorbed in the anodize coating is determined, and a value of the infrared energy absorbed in the anodize coating is correlated to an amount of the anodize coating.

According to an aspect of the invention, one embodiment of the invention includes transmitting an infrared beam having a predetermined wavelength through an anodize coating on a metallic substrate at a predetermined incident beam angle. The transmitted beam has a cross-sectioned area to produce a predetermined spot size on a surface of the anodize coating. The infrared beam is reflected off the metallic substrate to form a reflected beam and the reflected beam is filtered to a predetermined wavelength band, if desired, and detected. The infrared energy of the reflected beam is compared with a predetermined value of infrared energy reflected off the metallic substrate without the anodize coating to determine an absorbance value for the anodize coating. The absorbance value for the anodize coating is correlated to an amount of the anodize coating.

BRIEF DESCRIPTION OF THE DRAWINGS

The preferred and alternative embodiments of the present invention are described in detail below with reference to the following drawings.

DETAILED DESCRIPTION OF THE INVENTION

Figure 1:
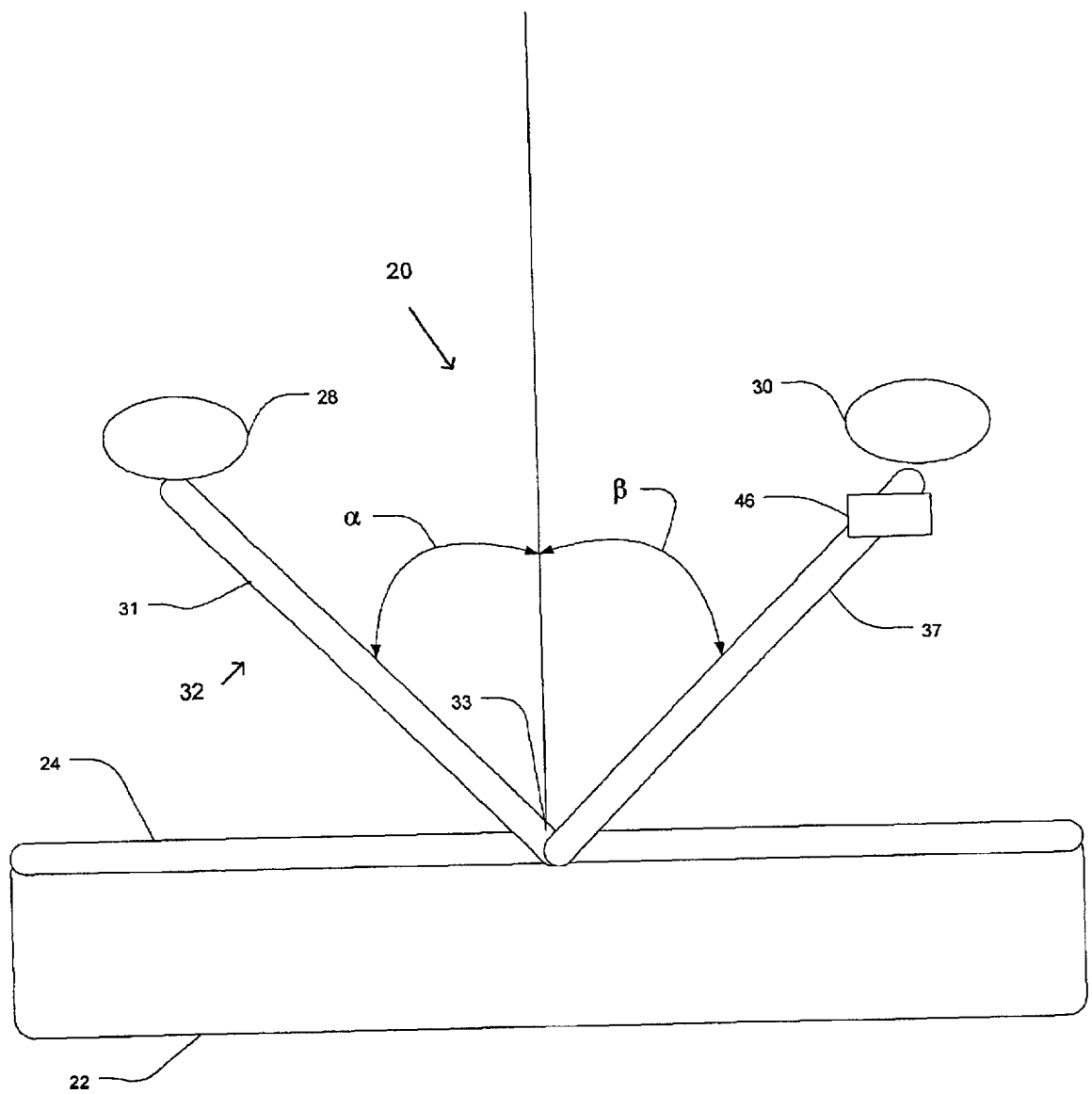
FIG. 1 is a side view of a testing setup according to the present invention.

The present invention provides a method for nondestructively determining an amount, either thickness or weight, of an anodize coating that has been formed on a metallic substrate by correlating the infrared absorbance of the coating, at a specific wavelength, to the coating amount. By way of overview and with reference to FIGS. 1 and 2, one presently preferred embodiment of the present invention determines anodize coating amount using a testing setup 20. Initially, a base reference value of infrared energy reflected by an uncoated metallic substrate is determined. An infrared transmission beam 31 is transmitted from an infrared source 28 along a predetermined incident beam path 32 through an anodize coating 24. The infrared beam 31 is transmitted in such a fashion to form a spot 33 having a predetermined size on the surface of the coating 24. The transmission beam 31 is reflected off a metallic substrate 22 to form a reflected beam 37. The reflected beam 37 is passed through the coating 24, is filtered to a predetermined wavelength, if desired, and is detected by an infrared detector 30. A comparison is made of the infrared energy of the reflected beam and the infrared energy of the base reference value to determine a coating absorbance value. The coating absorbance value is correlated to an anodize coating amount. Specific details of the testing setup 20 are described with more particularity below.

In one presently preferred embodiment, the measurement is conducted on a coating produced on a 2024-T3 bare aluminum alloy. However, other metallic substrates are considered within the scope of this invention, such as, without limitation, 2024-T3 clad aluminum alloy, 7075-T6 bare aluminum alloy and pure aluminum. Additionally, it will be appreciated that other aluminum alloys may be used without departing from the spirit of the invention.

The anodize coating 24 is preferably the result of a Boric Sulfuric Acid Anodize process. However, it will be appreciated that any other anodized coating process is considered within the scope of this invention. Non-limiting examples of other acceptable anodizing processes are Boric Sulfiuric Acid Anodize (BSAA), Sulfuric Acid Anodize, Phosphoric Acid Anodize (PAA) and Chromic Acid Anodize (CAA).

In one presently preferred embodiment, the testing setup 20 is suitably a simple infrared filter system, including an infrared generator, transmitter, filter, detector, and reflection optics. A non-limiting example of a simple infrared filter system is a Coating Weight Reader produced by Personal Instruments. However, it will be appreciated that other infrared systems are employable with the testing setup 20, such as, without limitation, standard infrared spectrometers and infrared imaging systems. Non-limiting examples of standard infrared spectrometers are a Thermo Nicolet 760 FT-IR spectrometer system fitted with a Spectra Tech FT-60 accessory and a Surface Optics Corporation SOC400 portable FT-IR spectrometer with a specular reflectance attachment. Non-limiting examples of infrared imaging systems employable with the present invention include ImageMax® produced by Nicolet. It will be appreciated that the various infrared systems may include those configured to be used an in-line production element or may include a portable, hand-held arrangement.

The infrared beam 31 is suitably transmitted as a broadband mid-infrared light beam (2.5 to 25 microns typically). In a preferred embodiment, the reflected beam 37 is suitably filtered by a filter 46 at a preferred wavelength band with a center wavelength of approximately 10.89 microns ($\mu$m). The filter 46 may act on either the transmitted beam 31 or the reflected beam. The target wavelength is characteristic of the primary Aluminum-Oxygen-Aluminum vibrational stretch. It will be appreciated, however, that the optimal wavelength may deviate from the preferred wavelength depending on the process employed to form the anodized coating 24. A wavelength within a range from about 10.6 $\mu$m to about 11.2 $\mu$m has been found to provide acceptable infrared absorbance characteristics and is to be considered within the scope of this invention. Further, it will be appreciated that, when using either the standard infrared spectrometer or infrared imaging systems, the filter 46 may suitably be implemented by either hardware or software performing the same filtering function. When the detected infrared beam 31 has a wavelength band within this disclosed range, a substantially linear relationship has been found to exist between infrared absorbance and the anodized coating amount, as discussed in more detail below.

The broadband infrared beam 31 is generated by the infrared source 28. The infrared source 28 is any acceptable source of infrared energy known in the art that can produce the infrared beam 31 having the desired wavelength region. One suitable example of a preferred embodiment of the infrared source is the ReflectIR-P1N source made by Ion Optics.

The infrared detector 30 in the filtered systems described here is suitably arranged to detect the reflected beam 37. One suitable example of a preferred embodiment of the infrared detector 30 is the Eltec Corp 406MAY-XXX where XXX indicates the filter that is used with the detector.

The infrared beam 31 defines the spot 33 on the surface of the anodize coating 24. The size of the spot 33 is predetermined by use of a mask and/or focusing optics in communication with the infrared source 28. In a presently preferred embodiment, the size of the spot 33 is preferably within a range of about 2 mm to about 35 mm in diameter. However, a size of the spot 33 that is either above or below the preferred range is considered within the scope of this invention.

The incident beam path 31 is directed such that the incident beam angle $\alpha$ is within a desired range. In one presently preferred embodiment, the incident beam angle $\alpha$, relative to normal, is preferably about 30 degrees to about 60 degrees. In one embodiment, the incident beam angle $\alpha$ is preferably about 45 degrees. A reflected beam angle $\beta$ equals the incident beam angle $\alpha$. As a result, the reflected beam angle $\beta$ is preferably within a range of about 30 degrees to about 60 degrees from normal. In one presently preferred embodiment, the reflected beam angle $\beta$ is preferably about 45 degrees.

Figure 2:
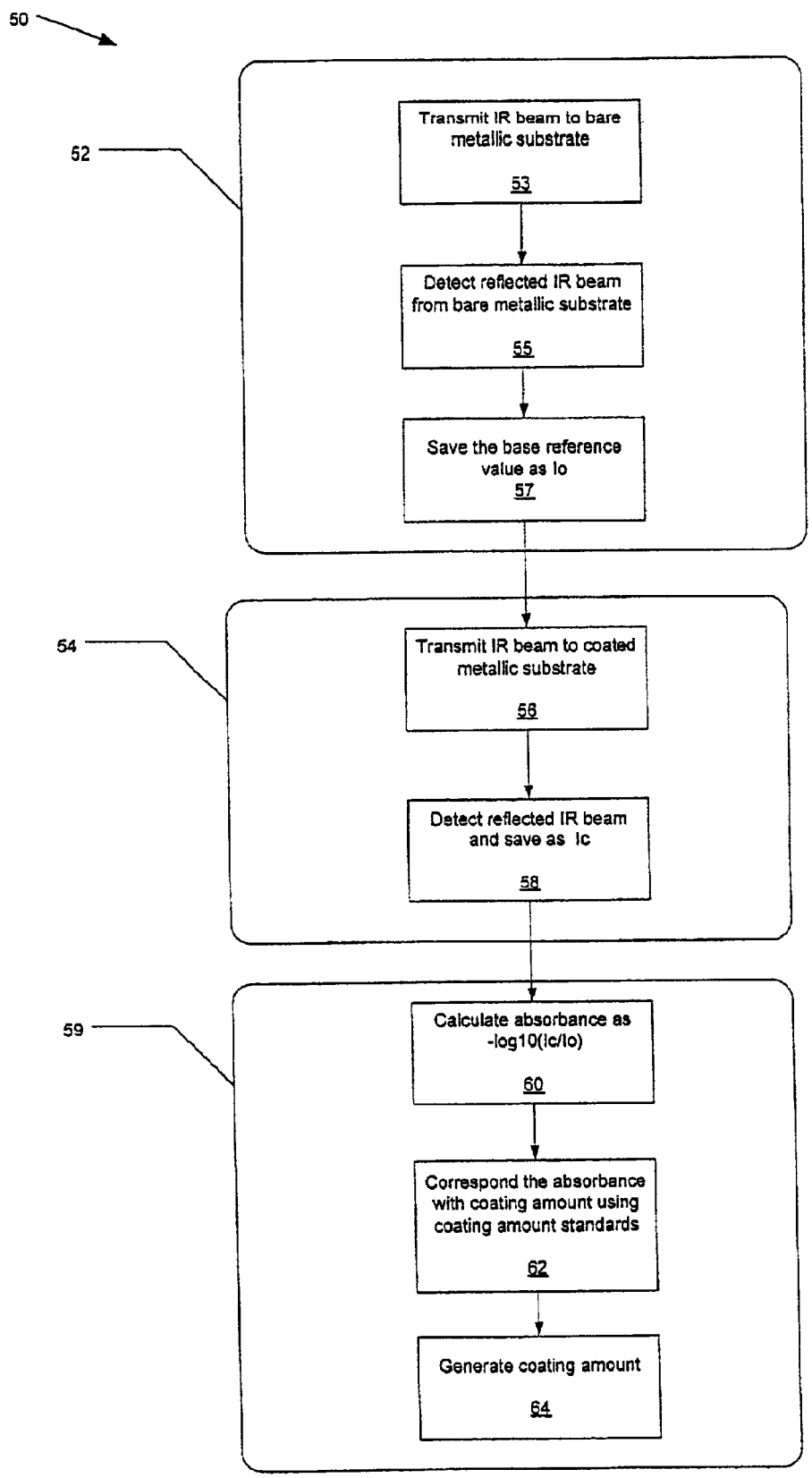
FIG. 2 is a flow chart of the testing process.

Referring now to FIGS. 1 and 2, a process 50 for determining the amount of an anodize coating is illustrated. This process is substantially the same for a filtered infrared beam system, a standard infrared spectrometer system or infrared imaging systems. An infrared energy base reference value $I_o$ is determined at block 52 for a non-coated metallic substrate of the same material to be tested to determine an amount of infrared energy occurring without the anodize coating 24. At a block 53, the infrared beam 31 is transmitted along the incident beam path 31. At a block 55, the reflected beam 37, at a specific wavelength, is detected to yield the base reference value, $I_o$. At a block 57 the reference energy value is saved as $I_o$.

After determining the base reference value $I_o$, data collection on material with the anodize coating begins at block 54. As discussed above, the transmission beam 31 is directed through the anodize coating 24 at block 56 and is reflected off the metal substrate 22 to form the reflected beam 37. The reflected beam 37 is detected at block 58 and this value is saved as infrared energy $I_c$ of the reflected beam 37. It will be appreciated that parameters such as incident beam angle $\alpha$, size of the spot 33, and overall incident beam path length are maintained substantially similar in both reference value determination and the coating amount absorbance value determination to limit potential errors.

A data calculation and compilation occurs at a block 59. The data compilation process includes calculation of the absorbance value of the coating at a block 60 using the formula absorbance $I_a = -\log_{10}(I_c/I_o)$ The compilation and calculation is suitably performed in a number of acceptable manners. For example, in one embodiment, it is performed by a processor or microprocessor (not shown) arranged to perform mathematical operations. Any processor known in the art is acceptable, without limitation, a Pentium®-series processor available from Intel Corporation or the like. The processor is suitably included within the infrared spectrometer and is also suitably provided as a stand-alone unit that is electrically connected to receive data from the infrared detector 30. Alternately, the calculation is performed by an electronic computer chip or is performed manually. The results of the calculation yield an absorbance value that corresponds to an anodize coating amount at a block 62.

The absorbance measurement is repeated for several metal coupons with anodize coatings that are made as standards for the particular metal substrate and anodize coating to be tested. These standards have different coating amounts that are made by controlling the immersion time in the anodize process line. Higher coating amount is generated by longer immersion time. The coating amount for each of the standards is found by weighing the coupon, stripping off the coating and re-weighing the coupon. The amount in mg/ft$^2$ is calculated for each coupon. At block 64, the anodize coating amount is generated. More specifically, a calibration is calculated for the anodize coating by doing a plot or linear regression of the coating amount values versus the absorbance values. This calibration can then be used to correlate coating amount directly from absorbance values for anodize coatings on metal surfaces.

Figure 3:
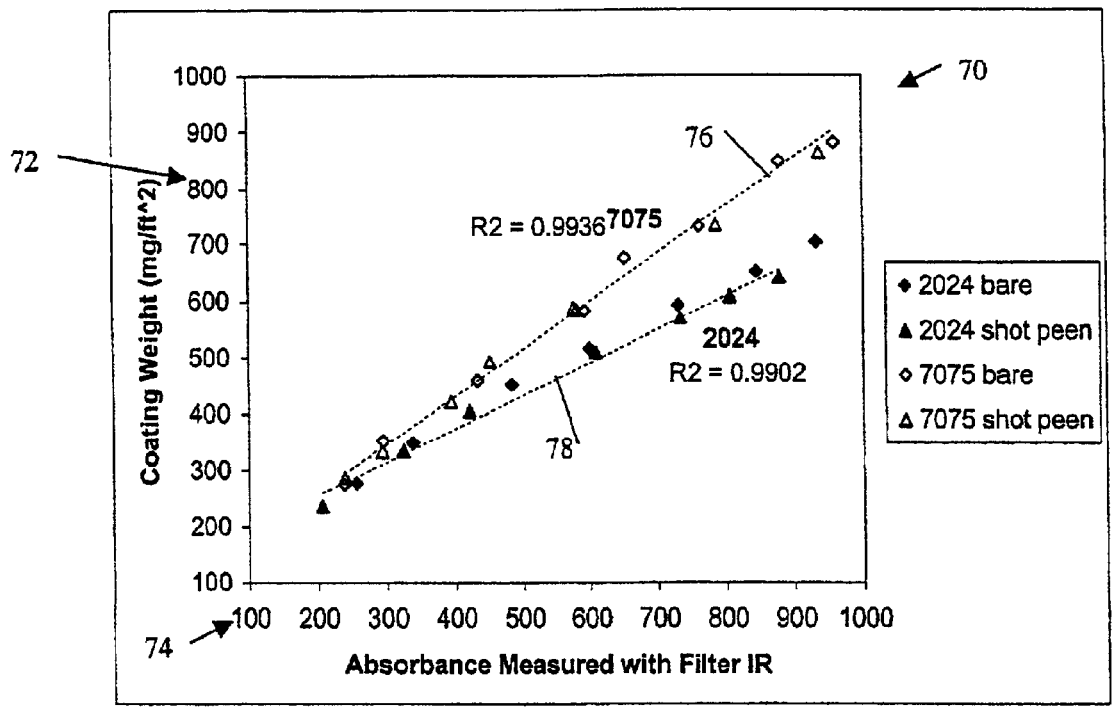
FIG. 3 is a graphical illustration of the relation between coating amount and infrared absorbance in accordance with the present invention.
Figure 4:
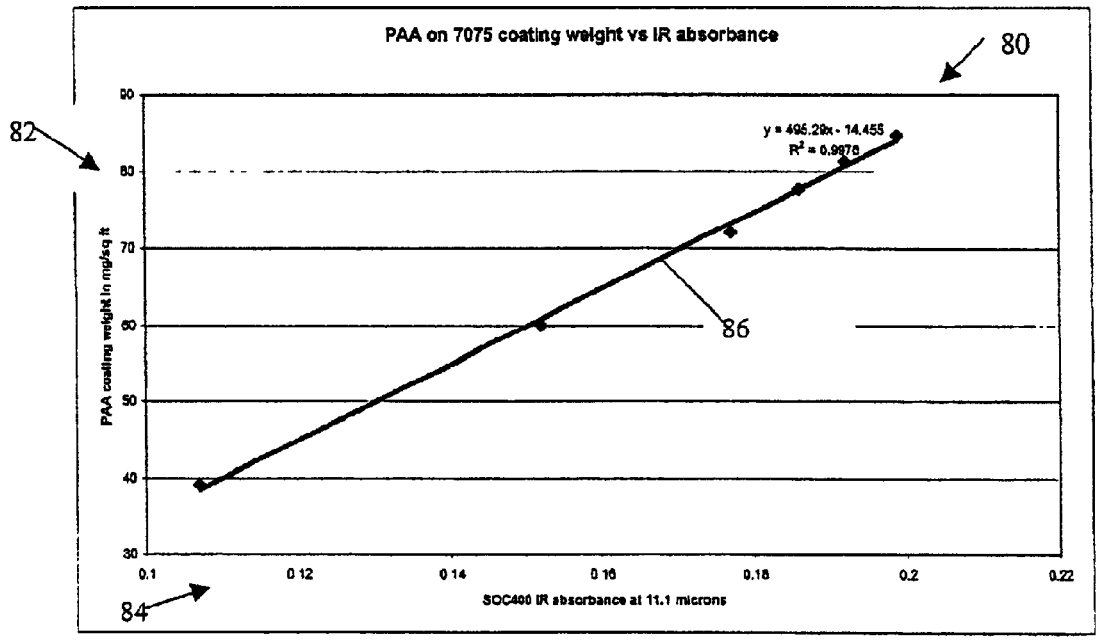
FIG. 4 is another graphical illustration of the relation between coating amount and infrared absorbance in accordance with the present invention.
Figure 5:
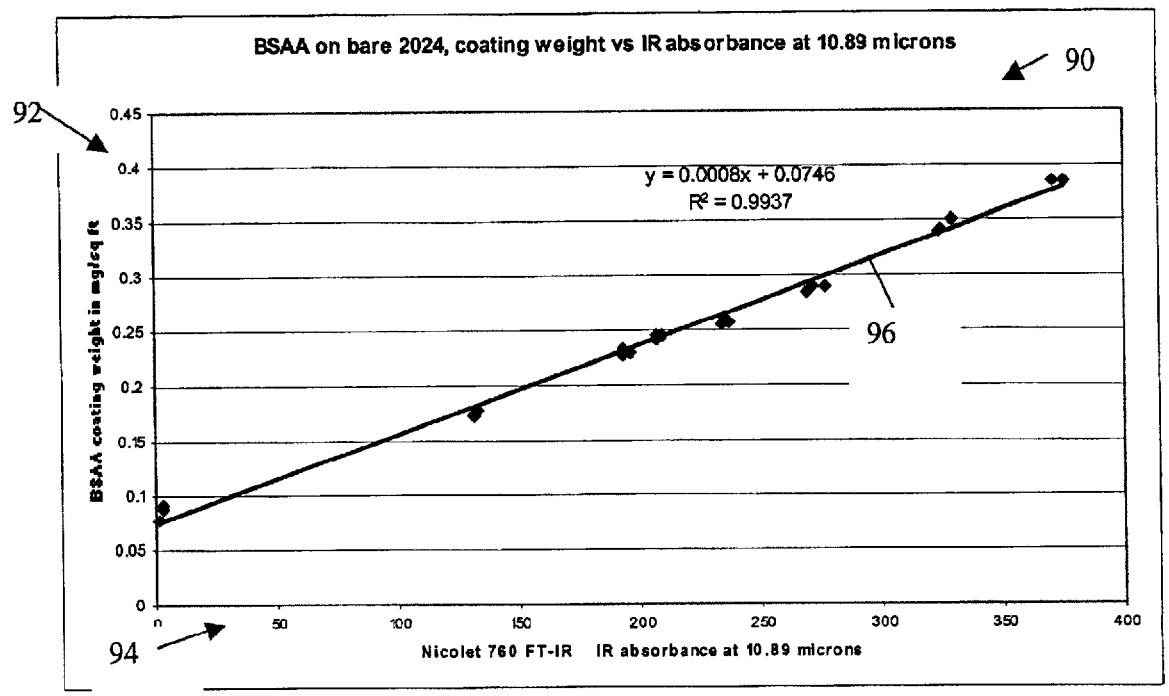
FIG. 5 is an additional graphical illustration of the relation between coating amount and infrared absorbance in accordance with the present invention.

FIGS. 3–5 depict the resulting test data illustrating the substantially linear relationship between the anodized coating amount and the infrared absorbance at the preferred wavelength. It will be appreciated that FIGS. 3–5 represent experimental data generated by different infrared spectrometer devices. However, each trial was performed by the process of the present invention. It will also be appreciated that prior to testing, both processes included making a base line determination according to the present invention.

FIG. 3 shows a graph 70 of mass of anodized coating along a vertical axis 72 versus infrared absorbance at a wavelength of 10.89 along a horizontal axis 74. The anodize system shown is Sulfuric Acid Anodize. The corresponding relationship between mass of anodized coating and infrared absorbance yield a substantially linear line 76 for tests on 7075 aluminum and line 78 for 2024 aluminum.

Experimental data displayed in FIG. 3 was collected using a prototype filter infrared spectrometer. This system uses a 55 degree reflection angle and a spot size of approximately 12.7 mm. The filter used has a 10.89 center wavelength and a bandwidth from 10.6 to 11.2 microns. The detector is lithium tantalite. The absorbance values are given in terms of actual absorbance times 1000 due to the way the data was processed by the built-in computer.

FIG. 4 shows a graph 80 of mass of a Phosphoric Acid Anodized coating along a vertical axis 82 versus infrared absorbance at a wavelength of 11.1 microns along a horizontal axis 84. The corresponding relationship between mass of anodized coating and infrared absorbance yield a substantially linear line 86.

Experimental data displayed in FIG. 4 was collected with a Surface Optics Corp. SOC 400 portable FTIR spectrometer. The SOC 400 spectrometer specular reflectance attachment was used with a 45 degree reflection geometry and a DTGS detector. The size of the spot 33 was approximately two millimeters in diameter. Data collection parameters included 64 scans, eight wavelength resolution, and a 2.5 to 25 micron wavelength range with software filtering to the appropriate absorbance band.

FIG. 5 shows a graph 90 of mass of Boric Sulfuric Acid anodized coating along a vertical axis 92 versus infrared absorbance at a wavelength of 10.89 microns along a horizontal axis 94. The corresponding relationship between mass of anodized coating and infrared absorbance yields a substantially linear line 96.

Experimental data displayed in FIG. 5 was collected using industry standard infrared spectrometry equipment. More specifically, a Thermo Nicolet 760 spectrometer was employed, fitted with a Spectra-Tech FT-60 reflectance accessory having a 60 degree reflection geometry. The FT-60 reflectance accessory was fitted with a half-inch circular mask to limit the area to a spot 33 with a diameter of 12.7 mm. The spectrometer system was set up with a deuterated triglycine sulfate (DTGS) detector, four-wave resolution, thirty-two scans for sample and reference, and a 2.5 to 25 micron wavelength spectral range. Each coupon was measured front and back in the center of the coupon.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A non-destructive method of determining an amount of anodize coating on a metallic substrate, the method comprising:

non-destructively determining a value $I_a$ of infrared energy at a predetermined wavelength within a range of about 10.6 microns to about 11.2 microns absorbed in an anodize coating on a metallic substrate; and correlating the value $I_a$ of the infrared energy absorbed in the anodize coating to an amount of the anodize coating.

2. The method of claim 1, further comprising:

determining a value $I_o$ of infrared energy reflected from the metallic substrate without the anodize coating.

3. The method of claim 2, further comprising:

determining a value $I_c$ of infrared energy reflected from the, metallic substrate having the anodize coating.

4. The method of claim 3, wherein non-destructively determining the infrared energy absorbed in the anodize coating is calculated according to the equation $$I_a = -\log_{10}(O_c/I_o).$$

5. The method of claim 1, wherein determining the value $I_a$ is performed during on-line manufacturing processing of the metallic substrate.

6. A non-destructive method of determining an amount of an anodize coating on a metallic substrate, the method comprising:

transmitting an infrared beam having a predetermined wavelength within a range of about 10.6 microns to about 11.2 microns through an anodize coating on a metallic substrate at a predetermined incident beam angle relative to normal, the transmitted beam having a cross-sectional area to produce a predetermined spot size on a surface of the anodize coating;

reflecting the infrared beam off the metallic substrate to form a reflected beam;

detecting the reflected beam;

comparing infrared energy $I_c$ of the reflected beam with a predetermined value of infrared energy $I_o$ reflected off the metallic substrate without the anodize coating to determine absorbance value $I_a$ for the anodize coating; and correlating the absorbance value $I_a$ for the anodize coating to an anodize coating amount.

7. The method of claim 6, wherein the predetermined spot size is in a range from about 2 mm to about 35 mm.

8. The method of claim 7, wherein the predetermined spot size is about 12.7 mm.

9. The method of claim 6, wherein the predetermined incident beam angle is in a range from about 30 degrees to about 60 degrees from normal.

10. The method of claim 9, wherein the predetermined incident beam angle is about 45 degrees from normal.

11. The method of claim 6, wherein the metallic substrate includes one of aluminum and an aluminum alloy.

12. The method of claim 11, wherein the aluminum alloy includes at least one of a 2024 aluminum alloy, a 6065 aluminum alloy, and a 7075 aluminum alloy.

13. The method of claim 6, wherein the anodize coating includes at least one of a Boric Sulfuric Acid Anodize, Thin Film Sulfuric Acid Anodize, Phosphoric Acid Anodize, and Chromic Acid Anodize.

14. The method of claim 6, wherein detecting the reflected beam is performed with an infrared spectrometer system.

15. The method of claim 6, wherein detecting the reflected beam is performed with an infrared filter system.

16. The method of claim 6, wherein detecting the reflected beam is performed with an infrared imaging system.

17. The method of claim 6, wherein the predetermined wavelength is about 10.89 microns.

18. The method of claim 6, wherein the absorbance value $I_a$ is calculated according to the equation $$I_a = -\log_{10}(I_c/I_o).$$

19. A non-destructive method of determining an amount of anodize coating on a metallic substrate, the method comprising:

transmitting an infrared beam having a predetermined wavelength within a range of about 10.6 microns to about 11.2 microns through an anodize coating on a metallic substrate at a predetermined incident beam angle in a range from about 30 degrees to about 60 degrees from normal, the transmitted beam having a cross-sectional area to produce a predetermined spot size in a range from about 2 mm to about 35 mm on a surface of the anodize coating;

reflecting the infrared beam off the metallic substrate to form a reflected beam;

detecting the reflected beam;

comparing infrared energy $I_c$ of the reflected beam with a predetermined value of infrared energy $I_o$ reflected off the metallic substrate without the anodize coating to determine an absorbance value $I_a$ for the anodize coating; and correlating the absorbance value $I_a$ for the anodize coating to an anodize coating amount.

20. The method of claim 19, wherein the absorbance value $I_a$ is calculated according to the equation $$I_a = -\log_{10}(I_c/I_o).$$

21. The method of claim 19, wherein the predetermined spot size is about 12.7 mm.

22. The method of claim 19, wherein the predetermined incident beam angle is about 45 degrees from normal.

23. The method of claim 19, wherein the anodize coating includes at least one of a Boric Sulfuric Acid Anodize, Thin Film Sulfuric Acid Anodize, Phosphoric Acid Anodize, and Chromic Acid Anodize.

24. The method of claim 19, wherein the predetermined wavelength is about 10.89 microns.

* * * * *